US009121808B2

(12) United States Patent
Leyte Guerrero et al.

(10) Patent No.: US 9,121,808 B2
(45) Date of Patent: Sep. 1, 2015

(54) PROCEDURE FOR THE DETERMINATION OF EFFECTIVE AND TOTAL POROSITY OF CARBONATED SEDIMENTARY ROCKS, AND MORPHOLOGY CHARACTERIZATION OF THEIR MICRO AND NANOPORES

(75) Inventors: Florentino Leyte Guerrero, Mexico City (MX); Vicente Garibay Febles, Mexico City (MX); Ubaldo Sadott Pacheco y Alcalá, Mexico City (MX); Eduardo Palacios González, Mexico City (MX); Gustavo Roberto Perez Lemus, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 871 days.

(21) Appl. No.: 13/353,615

(22) Filed: Jan. 19, 2012

(65) Prior Publication Data

US 2012/0197526 A1   Aug. 2, 2012

(30) Foreign Application Priority Data

Jan. 27, 2011   (MX) .................... MX/a/2011/001035

(51) Int. Cl.
    *G01V 5/00*     (2006.01)
    *G01N 23/04*    (2006.01)
    *G01N 15/08*    (2006.01)
    *G01V 5/02*     (2006.01)

(52) U.S. Cl.
    CPC .............. *G01N 23/04* (2013.01); *G01N 15/088* (2013.01); *G01N 23/046* (2013.01); *G01N 2015/0846* (2013.01); *G01N 2223/418* (2013.01); *G01N 2223/616* (2013.01); *G01N 2223/649* (2013.01); *G01V 5/02* (2013.01)

(58) Field of Classification Search
    USPC ......................................................... 250/253
    See application file for complete search history.

(56) References Cited

U.S. PATENT DOCUMENTS

| 4,146,788 A | * | 3/1979 | Mirkin et al. ................ 250/311 |
| 4,783,751 A | * | 11/1988 | Ehrlich et al. ................ 702/11 |
| 6,088,656 A | * | 7/2000 | Ramakrishnan et al. ....... 702/13 |
| 2008/0221800 A1 | * | 9/2008 | Gladkikh et al. .............. 702/11 |

(Continued)

OTHER PUBLICATIONS

Lucia, F.J., Petrophysical Parameters Estimated from Visual Descriptions of Carbonate Rocks: A Field Classification of Carbonate Pore Space, Journal of Petroleum Technology, 1983, vol. 216, pp. 221-224.

(Continued)

*Primary Examiner* — Christine Sung
(74) *Attorney, Agent, or Firm* — Roylance, Abrams, Berdo & Goodman, L.L.P.

(57) ABSTRACT

The present invention is concerned with a procedure to quantitatively determine both, total and effective porosity of carbonated sedimentary rocks, and is based on the elaboration of molds of the rock pores-structure and on the determination of the volumetric and gravimetric properties of the rock and its mold.
Determination of the effective porosity is achieved by using an original formula, developed by the authors of the present invention.
Additionally, the structure of micro and nanopores in the rock is characterized by scanning electron microscopy (SEM), to identify relevant properties for permeability analyzes such as: dimensions, shapes, type of connections, pore-structure patterns and pore throats. These and other parameters are used as indicators of the reservoir production and storage capacity.

24 Claims, 12 Drawing Sheets

(56) References Cited

U.S. PATENT DOCUMENTS

| | | | | |
|---|---|---|---|---|
| 2009/0103677 | A1* | 4/2009 | Wood et al. | 378/53 |
| 2011/0004447 | A1* | 1/2011 | Hurley et al. | 703/1 |
| 2013/0259190 | A1* | 10/2013 | Walls et al. | 378/9 |
| 2013/0301794 | A1* | 11/2013 | Grader et al. | 378/5 |
| 2014/0019054 | A1* | 1/2014 | De Prisco et al. | 702/12 |
| 2014/0067351 | A1* | 3/2014 | Gray et al. | 703/6 |
| 2014/0119497 | A1* | 5/2014 | Guzman et al. | 378/5 |
| 2015/0049784 | A1* | 2/2015 | Popov et al. | 374/44 |

OTHER PUBLICATIONS

Lucia, F.J., Rock-Fabric/Petrophysical Classification of Carbonate Pore Space for Reservoir Characterization, AAPG Bulletin (1995) vol. 79, No. 9, pp. 1275-1300.

Lucia, F.J., Carbonate Reservoir Characterization, Springer-Verlag, Berlin 1999.

Choquette, P.W. et al., Geologic Nomenclature and Classification of Porosity in Sedimentary Carbonates, AAPG Bulletin (1970) vol. 54, No. 2, pp. 207-250.

Lonoy, A., Making Sense of Carbonate Pore Systems, AAPG Bulletin (2006) vol. 90, No. 9, pp. 1381-1405.

Fatt, I., The Network Model of Porous Media, Petroleum Transactions AIME (1956) No. 207, pp. 160-181.

Wardlaw, N.C. et al., Geology of Carbonate Porosity, Short Course: Pore Systems in Carbonate Rocks and Their Influence on Hydrocarbon Recovery Efficiency, 1979, Houston, Texas.

Chatzis, I. et al., Modeling Pore Structure by 2-D and 3-D Networks with Applications to Sandstones, Journal of Canadian Petroleum Technology, 1977, pp. 97-108.

Chidsey, T.C., Heterogeneous Shallow-Shelf Carbonate Buildups in the Paradox Basin, Utah and Colorado: Targets for Increased Oil Production and Reserves Using Horizontal Drilling Techniques, Semi-Annual Technical Progress Report (2002) Utah Geological Survey.

Cantrell, D.L. et al., Microporosity in Arab Formation Carbonates, Saudi Arabia, GeoArabia (1999) vol. 4, No. 2, pp. 129-154.

Walker, B.M., Chalk Pore Geometry Using Resin Pore Casts, Proc. of the Scanning Electron Microscopy in the Study of Sediments a Symposium, Edit. Whalley, W. B., published by GeoAbstracts (1978) Norwich, England.

Lin, C. et al., Pore Geometry: A New System for Quantitative Analysis and 3-D Display, Journal of Sedimentary Research (1983) vol. 53, pp. 670-672.

Nutting, P.G., Some Physical Problems in Oil Recovery, Oil and Gas Journal (1929) vol. 28, No. 27, pp. 44-45.

Waldo, A.W. et al., Method of Impregnating Porous Materials to Facilitate Pore Studies, AAPG Bulletin (1937) vol. 21, No. 2.

Wardlaw, N.C., Pore Geometry of Carbonate Rocks as Revealed by Pore Casts and Capillary Pressure, The American Association of Petroleum Geologists Bulletin (1976) vol. 6, No. 2, pp. 245-257.

Pittman, E.D., Porosity, Diagenesis and Productive Capability of Sandstone Reservoirs, Aspects of Diagenesis, Society of Economic Paleontologists and Mineralogists Special Publication (1979) No. 26, pp. 159-173.

Patsoules, M.G. et al., A Quantitative Analysis of Chalk Pore Geometry Using Resin Casts, Energy Sources (1993) vol. 7, No. 1.

Reed, S.J., Electron Microprobe Analysis and Scanning Electron Microscopy in Geology, Cambridge University Press (1996).

Rigby, S.P., Structural Models for the Interpretation of Nitrogen Adsorption and Mercury Porosimetry Data, Encyclopedia of Surface and Colloid Science, Somasundaran, P., Ed. 2nd. (2006) Pub. CRC Press.

Zinszner, B. et al., A Geoscientist's Guide to Petrophysics, Translated by Trevor Jones, Published by Editions Ophrys (2007).

* cited by examiner

PROCEDURE FOR THE DETERMINATION OF EFFECTIVE AND TOTAL POROSITY OF CARBONATED SEDIMENTARY ROCKS, AND MORPHOLOGY CHARACTERIZATION OF THEIR MICRO AND NANOPORES

FIELD OF THE INVENTION

The present invention is related to a procedure for quantitatively determine both, effective and total porosity of carbonated sedimentary rocks. The procedure is based on their volumetric and gravimetric properties. Additional to it, the morphological characterization of their micro and nanopores (determination of shapes, dimensions and pores-network distribution) is done by applying scanning electron microscopy (SEM) techniques.

BACKGROUND TO THE INVENTION

A reservoir is generically defined as:
  A concentration of elements or materials meaningful to some type of science; or
  The part of a geological trap containing oil, gas or both, which behaves as a hydraulic networked system.

A reservoir, in the oil and gas industry and according to the Oilfield glossary by Schlumberger, is an underground geological body that has enough porosity and permeability to store and transport fluids.

A hydrocarbons reservoir, in this context, is a geological body in which there is an accumulation of a meaningful volume of hydrocarbons.

In order to be able to store hydrocarbons in a reservoir, the containing overlaying and underlying strata must be impermeable enough to avoid fluids migration. Also the sides must prevent the leaking of fluids.

Particular conditions must be present for an oil or gas field to exist, among them: rock porosity, defined as the ratio from pores to total volume of the rock, i.e., the voids not occupied by the rock's mineral skeleton; another more convincing definition is the storage capacity that a rock has, estimated by the fields reservoir's extension and average thickness, and by the occurrence of hydrocarbons given by the saturation degree, which is the fraction of the porous volume occupied by the a given fluid.

The above factors are useful to estimate the reservoir's volumetric aspect. To complete this aspect, it is required to determine and apply the production factor. Therefore, and according to the above, it is concluded that both, the following productive life of the reservoir and the economical aspect of initial development are closely related to the extraction factor, which represents an estimate of the amount of oil/gas that can be produced during the reservoir's primary production period.

Rock permeability is also another important factor to point out. This is the rock's ability to allow fluids to flow through its interconnected pores. In this context is it relevant to observe that the effective porosity is the fraction of continuous pores which are interconnected, which contribute to the fluid transport through a rock or sediment, not including the isolated pores and pores with closed endings.

There can be permeability variations in a reservoir, both, vertically and laterally. Considering a stratified rock, the measured permeability along the stratification planes is called horizontal permeability. Permeability depends upon the grain size uniformity (selectivity), grains shape, deposition regime (packing), mechanical compaction, dissolution and cementation.

There is not a mathematical correlation between porosity and permeability. They both are obtained through sampled cores, tested in the lab, or by interpretation of specific recordings done directly along the geological column in the well.

Fluids in the reservoir move towards the existing wells due to the rock-fluid system expansion, when the internal pressure drops, by natural or artificial displacement (by gas or water injection), by gravity induced drainage and/or by capillary phenomena.

Hydrocarbon Reservoirs and Reserves Classification

Hydrocarbon reservoirs (oil) have been grouped attending to a number of factors such as:
  Reservoir rock's nature.
  Trap type.
  Nature of the existing fluids.
  Original pressure.
  Dominant pressure type.
  Phases diagram.
  According to the Reservoir Rock
  Sands. Their porosity is due to the fragments texture; they can be clean or unclean sands, they are ooze, silt, lignite, bentonite, etcetera.
  Ditritic limestone, formed by aggregation of limestone fragments or dolomite fragments.
  Porous crystalline limestone; their porosity is attributed mainly to dissolution phenomena.
  Fractured limestone. Their porosity is mainly due to the existence of fractures.
  Oolitic limestone. Their porosity is due to their oolitic texture, with non-cemented or partially cemented interstitial voids.
  Sandstones, they are highly cemented sands, the cements can be calcareous, dolomitized, clayey, etcetera.

Carbonated reservoirs can be colossal, with microscopic porosity and very low permeability, but the fluids flow through their fractures system.

Carbonates and composed by a limited group of minerals, mainly calcite and dolomite. Other less abundant minerals are phosphates and glauconite.

Sedimentary Carbonated rocks differ from sedimentary siliciclastic rocks in several aspects. Siliciclastic rocks are formed either as the sediments are transported, deposited and lithified, or when the sediments are compacted and cemented into a solid rock; On the contrary, carbonated rocks are developed through biogenetic sediments, formed by geologic activity, such as formation of reefs and accumulation of organic detritus on the seabed.

Carbonated rocks differ from clastic rocks in factors such as depositional texture, grain or pore types, rock composition or diagenesis (Process in which a rock is formed from loosed sediments subjected to compaction phenomena), since clastic rocks can be distinguished by their composition and grain size distribution.

Carbonates diagenesis can meaningfully modify both, permeability and the space between pores.

Carbonated rocks are highly diagenetic as a consequence of the fast instability of his components underground.

According to the above, it is important to consider the following concepts:
  A pores system is made of large voids called "pores", which are connected by smaller voids or contractures called "pore throats".
  Effective porosity is considered as the volume fraction of the total voids volume inside the rock, made of interconnected continuous pores, not including isolated and/or pores with a blind end, which contributes the fluid's flow through the rock or sediment.

Microporosity is observed in regions of the earth where hydrocarbons are stored, often in carbonated or sandy rocks, these regions are called reservoirs.

Hydrocarbons recovery efficiency depends upon the fluid's properties and the pores-system characteristics of the reservoir.

Measurement of porosity and associated parameters, such as pore and throat size, geometry, size distribution, pore/throat ratio, quality and interconnectivity are relevant for the estimation of both, storage and flow capacity (potential production) in hydrocarbons fields; also, they provide relevant information to perform other kind of evaluations such as potential directions of drilling.

Porosity above then microns has been thoroughly studied; models and methods have been developed to study it from both, qualitative and quantitative standpoints, according to the following references:

Lucia, F. J. "Petrophysical Parameters Estimated from Visual descriptions of Carbonate Rocks: A Field Classification of Carbonate Pore Space.", Journal of Petroleum Technology 1983, V. 216, pp. 221-224;

Lucia, F. J. "Rock-Fabric/petrophysical Classification of Carbonate Pore Space for Reservoir Characterization.", AAPG 1995, Bulletin V. 79, No. 9, pp. 1275-1300;

Lucia, F. J. "Carbonate Reservoir Characterization.", Springer-Verlag, Berlin 1999;

Choquette, P. W., y Pray, L. C. "Geologic Nomenclature and Classification of Porosity in Sedimentary Carbonates", AAPG 1970, Bulletin V. 54, No. 2, pp. 207-250; y Lonoy, A. "Making Sense of Carbonate Pore Systems", AAPG 2006, Bulletin V. 90, No. 9. September 2006. pp. 1381-1405.

However, porosities below ten microns, already difficult to observe, are even harder to study. The most remarkable efforts in this regard are the development of characterization and measurement systems by thin sheets, firmly supported by optic microscopy and imaging oriented software.

Microporosity is the fraction of porosity below ten (10) microns; effective porosity is the fraction of microporosity, which has continuous interconnected pores, not including isolated pores and/or pores with blind endings.

The relevance of both, quantitative evaluation of effective microporosity and its microstructural characterization is manifested in the following facts:

Fatt, I. in his work "The Network Model of Porous Media.", Petroleum Transactions, AIME 1956, No. 207, pp. 160-181, shows that the interconnectivity in a rock porous system is relevant to the recovery efficiency (RE), and concludes that RE increases as the coordination number increases. The coordination number is defined as the number of pore throats connected to each pore in an infinite-sized network of pores.

Wardlaw, N. C. in "Geology of Carbonate Porosity", Short Course: Pore Systems in Carbonate Rocks and Their Influence on Hydrocarbon Recovery Efficiency. April 1st. 1979, Huston, Tex., provides evidence to affirm that as both, the pore/throat ratio and the volumes ratio increase, the recovery decreases, and Observations made by Chatzis, I. and Dullien, F. A. L. in "Modeling Pore Structure by 2-D and 3-D Networks with Applications to Sandstones.", Journal of Canadian Petroleum Technology. March 1977, pp. 97-10, allow them to conclude that residual saturation in a non-wettable phase increases, i.e., recovery efficiency decreases as the coordination number decreases.

So far, there is not a well know relationship between macro and microporosity; efforts geared towards that end will play a fundamental roll in reservoirs modeling, through the inclusion of the matrix porosity characteristics into the macroporosity, leading to a more reliable and precise predictions; a first step forward, after macroporosity determination, is to know and be able to characterize microporosity, particularly effective microporosity.

Chidsey, T. C., points out that the knowledge of the porosity types by resin injection of rocks and the diagenetic sequences found, along with the materials and cements observed in the porous systems in reservoir rocks, may reveal the flow capacity of a reservoir; this in his technical paper "Heterogeneous Shallow-Shelf Carbonate Buildups in the Paradox Basin, Utah and Colorado: Targets for Increased Oil Production and Reserves Using Horizontal Drilling Techniques.", Semi-annual Technical Progress Report. April, 2002-Oct. 5, 2002. Utah Geological Survey.

Cantrell, D. L., and Hagerty, R. M., in their paper "Microporosity in Arab Formation Carbonates, Saudi Arabia.", GeoArabia 1999, Vol. 4, No. 2 paper, present a study on the microporosity distribution in Arab carbonates, indicating that the development of maps and transverse sections showing textural variations in the reservoir along with the texture and microporosity relations obtained in their study, may be effective tools to explain and predict the fluids flow, well response and ultimately the behavior of the reservoir.

Very few researchers have mentioned the "effective porosity" at the micro and nanometric level; among them Walker, B. M. in his paper "Chalk Pore Geometry Using Resin Pore Casts.", Proc. of the Scanning Electron Microscopy in the Study of Sediments a Symposium. Edit. Whalley, W. B., published by Geo Abstracts in 1978, Norwich, England, and much less invested their efforts to determine it, such as Lin, C., and Hamasaki, J. in "Pore Geometry: A New System for Quantitative Analysis and 3-D Display", Journal of Sedimentary Research 1983, 53: 670-672.

Although by 1983, Lin et al., presented a novel technique, a second impregnation modifies the morphological properties of the pores network. Besides, the process is slow and requires many microtomes sections to obtain a realistic computerized model, then it is needed to obtain good quality images of each section, magnify and process them numerically, which is a lengthy and imprecise process since, in complex porosity systems, many details of connections among pores, lengths and sizes can be altered, finally the model turns into an inaccurate representation of the system.

Wardlaw, N. C. in his paper "Geology of Carbonate Porosity", Short Course: Pore Systems in Carbonate Rocks and Their Influence on Hydrocarbon Recovery Efficiency. April 1st. 1979, Huston, Tex., proposes an indirect process to evaluate the potential rocks reservoir production through the morphological characterization of the porous network, obtained by injection of resin into the rock, however this method does not consider the effective porosity.

On the other hand, a number of techniques to produce porosity casts have been used in the past, among them the following:

Nutting P. G. in his paper "Some physical problems in oils recovery" Oil and Gas Journal, 28(27), 1929, Pp. 44-45, performed a pioneering work, using an injection procedure, to study porosity.

Waldo, A. W., and Yuster, S. T. report the use of a melted balm, added with oil-based paint, to inject the pores in vacuum environment, the samples then were examined in thin sections. This is reported in "Method of Impregnating Porous Materials to Facilitate Pore Studies", AAPG 1937, Bulletin V. 21.

Pittman, E. D., and Duschatko, R. W. present a state of the art on rocks injection techniques available by 1970. They also make a general description on epoxy-resin injection as well as the rock dilution using different substances, which depends on the rocks nature, i.e., carbonated materials or materials containing silicates. They recommend Hydrochloric acid (HCl) for those and Hydrofluoric acid (HF) for these. Also, for those materials having both, carbonated and silicated materials coexisting, they recommend first the dilution with HCl and then with HF, since carbonates react with HF producing calcium fluorides which are insoluble. They also include some example-images of pore structure resin castings, obtained from carbonated sediments and orthoquartzite, scanning electron microscopy images and a characterization based on them. They conclude highlighting the relevance of pore castings to provide important information on the genesis, distribution, pore and throat shapes in samples of carbonated and silicated rocks.

Wardlaw, N. C. in his paper "Pore Geometry of Carbonate Rocks as Revealed by Pore Casts and Capillary Pressure", The American Association of Petroleum Geologists Bulletin. Vol. 6 No. 2, February 1976. Pp. 245-257, describes pores geometry and pore/throat connections from a selected group of carbonated rocks, using the pores resin injection technique. Additional information on pore throat size distribution was obtained using Mercury Injection Capillary Pressure Analysis. Wardlaw also describes the pore systems in dolomites and siltstones, and discusses the Dolomite Crystals growth kinetics and its implications on porosity and permeability. This is accomplished by the use of micrographs obtained from their resin-casted pore networks; such characterization includes pore-network patterns, and pores and throats shapes and sizes.

Walker, B. M., in his work "Chalk Pore Geometry Using Resin Pore Casts.", Proc. of the Scanning Electron Microscopy in the Study of Sediments a Symposium. Edit. Whalley, W. B., Published by Geo Abstracts in 1978, Norwich, England, describes a number of techniques developed (up to 1978) to produce effective-porosity resin casts of calcareous rocks, those techniques include: wax impregnation, Wood's metal and epoxy resins. The advantages are evident when the samples are observed by scanning electron microscopy (SEM) techniques, larger depth of field and larger magnification capacity and resolution make of SEM techniques very appropriate to study the pores network in three dimensions. The latest is related to the rock physical and engineering properties and to sedimentology processes involved.

Pittman, E. D. in his technical paper "Porosity, Diagenesis and Productive Capability of Sandstone Reservoirs", in the book Aspects of Diagenesis. Society of Economic Paleontologists and Mineralogists Special Publication No. 26, pp. 159-173. March 1979, studies porosity, diagenesis and sandstones production capacity; here, he discusses four types of porosity: intergranular, by dissolution, microporosity, by fractures, and a combination of them. Resin impregnation techniques on rocks are used to study different types of pores structures, pores interconnections and pores sizes.

Wardlaw, N. C. in his work "Geology of Carbonate Porosity", Short Course: Pore Systems in Carbonate Rocks and Their Influence on Hydrocarbon Recovery Efficiency. April 1st. 1979, Huston, Tex., presents a procedure for hydrocarbons recovery efficiency estimation, this method is based on the determination of both, pores and pores-structure properties in carbonated reservoir rocks samples. The properties include pores geometries, rock-fluid and fluid-fluid interactions. His paper focuses on the determination of those pores-systems properties affecting the recovery efficiency of the non-wetting phase restricted by capillary forces. It is assumed a normal configuration integrated by a water wetting phase, and an oil non-wetting phase. The chief thesis here is that and estimation of the hydrocarbons recovery efficiency can be done by visual examination of the resin-casts obtained from the pores systems. The molds of their pores-structures were obtained by injection of resin in rocks under vacuum, then the rock samples are dissolved. Once the molds were obtained, three parameters were studied on the molds, namely: pore/throat ratio, b) throat/pore coordination number and c) type and degree of heterogeneity. From here, the structures are classified in four typical groups. Examples of these parameters are presented; then these are applied to a hydrocarbons recovery efficiency estimation. The results are compared with efficiency estimations obtained by Hg methods; the final conclusion is that the pore cast based recovery estimation method is ±10% off the Hg method.

Lin, C., y Hamasaki, J. in their work "Pore Geometry: A New System for Quantitative Analysis and 3-D Display", Journal of Sedimentary Research 1983, 53: 670-672, present a variation of the pore casting technique, which includes a double resin impregnation. Here, when the first resin cast is obtained, and after rock dissolution, a second impregnation of Bromine-doped resin provides contrast density for the cast to be observed by scanning electron microscopy (SEM). This technique includes to microtome-slice the casted resin to 5 to 10 microns thick slices. Then, they are mounted on a SEM-sample holder, each single slice is shot and its image magnified to the required scale; next, the set of images are computer processed by a custom made image-analysis software and integrated in a three dimensional virtual object; this object, according to the authors, represents the pore network system, it can be shown in colors, rotated or digitally sliced in any orientation and be photographed to create panoramic views.

Patsoules, M. G., and Cripps, J. C. in their work "A Quantitative Analysis of Chalk Pore Geometry Using Resin Casts.", Energy Sources 1993, Vol. 7, No. 1. 0090-8312/83010015-00$02.00/0, describe historically the invention and development of pore-cast techniques and discuss on the materials used to impregnate the samples tested. Beginning with the need of drying the specimens for at least three days; they describe in detail the process of fluid penetration in rocks, then the resin curing. Next, they explain the rock dissolution, underlining that the observed dissolution slowdown is due to the damage caused to the smallest parts of the resin cast; next, the molds are deionized-water washed, dried and prepared to be observed by SEM. The authors indicate that they did not used hydrofluoric acid to dilute the remaining silicates since they can easily be observed in the resin cast; besides, the casted pore network can be damaged. Patsoules and Cripps include, supported in their analysis from SEM micrographs, the coordination number; this number was originally used by Wardlaw (1979). They also present pores size distribution charts, based on measurements done on stereoscopic images, and present the size ranges of these pores, also describing morphologically the existing types of pores.

In their discussion, they establish the relevance of pores sizes in the hydrocarbons flow potential of reservoirs. Then, when those parameters are introduced, the rock porosity is quantitatively described by including:
a. Pore/throat ratio
b. Throat/pore coordination number
c. Type and degree of heterogeneity
d. Pores and grains roughness
e. Total number of pores and grains in the specimen
f. Total volume of pores and grains in the specimen
g. Total surface area of pores and grains
h. Pores and grains roundness
i. Mineral cleavage
j. Discoidal-pores orientation.

Reed, S. J. B. in his work "Electron Microprobe Analysis and Scanning Electron Microscopy in Geology", Cambridge University Press 1996, briefly describe the resin-cast technique applied to geological samples, its uses, the resin's desirable properties and some procedures to improve impregnation efficiency; he also describes the procedure to obtain pore casts of rocks, providing references to obtain details of this technique, applied to calcareous samples; finally, he describe the use of latex to obtain molds of fossilized plants, in order to study topographic details, which applied in several layers is strong enough to withhold vacuum, sputtering and electrons bombarding when observed by SEM.

Cantrell, D. L., and Hagerty, R. M. in "Microporosity in Arab Formation Carbonates, Saudi Arabia.", GeoArabia 1999, Vol. 4, No. 2, present a description on the occurrence, distribution, abundance and origin of meaningful amounts of microporosity in Saudi Arabia Formations. This study proposes, in the first place, a definition of microporosity based on the light-microscopy resolution limit, established as 10 microns, so that "microporosity" is defined as the one having pore diameters below ten (10) microns; later, they propose a porosity classification system based in four (4) dominant patterns, observed in the formations studied by resin-casts and SEM. The latest technique allowed determining the porosity existing types and their interconnections, internal structure, average diameter of pores, pore throats and their interconnectivity. The abundance and variability of microporosity was estimated in two ways: first, by point counting in thin sheets and by Hg injection techniques. This allowed comparing microporosity as a fraction of the total porosity versus the Hg measured porosity.

Chidsey, T. C. in his work "Heterogeneous Shallow-Shelf Carbonate Buildups in the Paradox Basin, Utah and Colorado: Targets for Increased Oil Production and Reserves Using Horizontal Drilling Techniques.", Semi-annual Technical Progress Report. April, 2002-Oct. 5, 2002. Utah Geological Survey, discuss on the characterization and evaluation of near one hundred (100) oil fields in the Utah Paradox Basin, Arizona, New Mexico, with the aim of performing lateral horizontal drills from existing wells. The above characterization was done using representative rock cores, geophysical logs, thin sections, Hg injection testing, samples pore-casts and SEM techniques. In this context, SEM analysis of pore-casts and the rock samples themselves allowed to describe the different porosity patterns and the diagenetic sequences found, types of materials and cements observed in the pores of the reservoir rocks at Cherokee and Bug Fields. Chidsey points out that these variables are potential indicators of the reservoir flow capacity, storage capacity and potential for horizontal drilling.

Rigby, S. P. in his document "Structural Models for the Interpretation of Nitrogen Adsorption and Mercury Porosimetry Data.", Encyclopedia of surface and colloid science, Somasundaran, P., Ed. 2nd. 2006, Pub. CRC Press. ISBN 0849396042, 9780849396045 6775, basically describes the technique used by Lin et al in 1983, where a double impregnation ad rock dissolution are used in order to obtain pores-casts, then the rock pore system is reconstructed from both, experimental measurements of thin sections using SEM techniques and a correlation function applied to the set of sections-images obtained sequentially.

Zinszner, B., and Pellerin, F-M., in their paper "A Geoscientist's Guide to Petrophysics", Translated by Trevor Jones Published by Editions Ophrys 2007, ISBN 2710808994, 9782710808992, devote a whole chapter to discuss the existing techniques to study rocks-pores networks. Their document include materials used for this purpose, such as epoxy resins, Metil Metacrilato (Plexiglass, Lucite), handling and care, pros and cons. In their discussion on physical parameters affecting impregnation quality, they include a procedure based on Washburn equation to calculate the depth of resin penetration. The penetration efficiency is demonstrated through SEM micrographs obtained from microfossils and their equivalent resin-casts. Zinszner and Pellerin propose a procedure to obtain resin-molds of rocks containing both carbonates and silicates; first, treating the sample with Hydrochloric Acid (HCl) and then with Hydrofluoric Acid (HF), they emphasize the need of use extreme caution handling the latest acid since it is harmful to whom does not know how to handle it. They punctually mention that the existence of calcium-silicates pose a problem for which they do not offer a practical solution, since the low solubility of calcium fluoride produced in the reaction is deposited directly in the preparation; they also indicate that this problem is present in some clays or sandstones rich in calcic feldspars. Their presentation includes stereomicroscopy of resin-casts, a very little used observation technique, which provides a quasi three dimensional view of the pores: to use this technique it is required to obtain pairs of micrographs of the same region, tilted each other from 5 to 10 degrees. These images should be observed with a stereoscopic microscope. They alternatively propose the use of metal Wood for Rocks pores injection, discuss its pros and cons and possibilities and limitations.

According to the state of the art, resin casts procedures to study rocks porosities and their applications, have experienced very little change. Direct applications of this technique are focused on morphologic characterization of microporosity networks of both hydrocarbons storing and producing rocks, however very little has been done on the determination of their volumetric and gravimetric properties.

The above technique limitations, known by Applicants, are overcome by the present invention, since none of the cited publications is integrally related to a procedure to quantitatively determine both effective and total microporosity of carbonated sedimentary rocks, and the morphological characterization of their micro and nanopores by scanning electron microscopy techniques (SEM).

It is, therefore, an object of the present invention to provide a procedure to quantitatively determine both, total and effective porosity of carbonated sedimentary rocks, through their volumetric and gravimetric properties.

An additional object of the present invention is to provide a procedure to morphologically characterize the micro and nanopores of carbonated sedimentary rocks, i.e., to determine shape, dimension and distribution of the pore network of carbonated sedimentary rocks, applying scanning electro microscopy techniques (SEM).

SUMMARY OF THE INVENTION

A process to quantitatively determine effective and total porosity of carbonated sedimentary rocks, and morphologic characterization of their micro and nanopores has been developed, which process comprises obtaining specimens of carbonated sedimentary rock and subjecting the carbonated sedimentary rock specimens to:
  a. Determining rock dissolution factor (FDR) of a carbonated sedimentary rock specimen,
  b. Trimming a carbonated sedimentary rock specimen to obtain a trimmed rock specimen,
  c. Cleaning the trimmed rock specimen to obtain a cleaned rock specimen,
  d. Drying the cleaned rock specimen to obtain a dried rock specimen,
  e. Inspection of the cleaned rock specimen to obtain an inspected rock specimen,
  f. Marking of the cleaned rock specimen for orientation to form a marked rock specimen,
  g. Injecting a resin into the marked rock specimen to form a resin-injected rock specimen,
  h. Trimming the resin injected rock specimen,
  i. Framing of the resin injected rock specimen,
  j. Dissolving the resin injected rock specimen to form a pore network specimen having a resinous pore structure,
  k. Washing the pore network specimen and collecting the solid residues containing non-connected pores-casts and existing fines material, and drying the pore network specimen,
  l. Separating the non-connected pores-casts from the existing fine material, and determining the mass of the non-connected pores-casts and of the existing fine material,
  m. Measurement of the pore structure properties of the pore network specimen,
  n. Determination of effective and total porosity of the pore network specimen ($\eta_E$ and $\eta_T$),
  o. Sputtering of the pore network specimen, and
  p. Analysis of the pore network specimen with scanning electron microscopy to characterize the porosity of the pore network specimen in the range of scale sizes from micrometric to nanometric.

According to one embodiment of the invention, the resin-injected rock specimen is dissolved in step (j) with HCl and/or HF.

According to another embodiment of the invention, step (a) comprises acid dissolution or digestion of the specimen using 15 to 25 ml of concentrated HCl, at 60 to 70° C. temperature and magnetic shaking for 20 to 40 minutes until the rock is completely dissolved to obtain a rock solution, the rock solution is filtered to obtain separated solids, which separated solids are water washed, dried and weighed, and the rock dilution factor (FDR) of the separated solids is determined by the formulae % of Insoluble material in HCl=(residues weight/sample weight)*100 and

FDR=100−% Insoluble material in HCl.

DETAILED DESCRIPTION OF THE INVENTION

Figure 1:
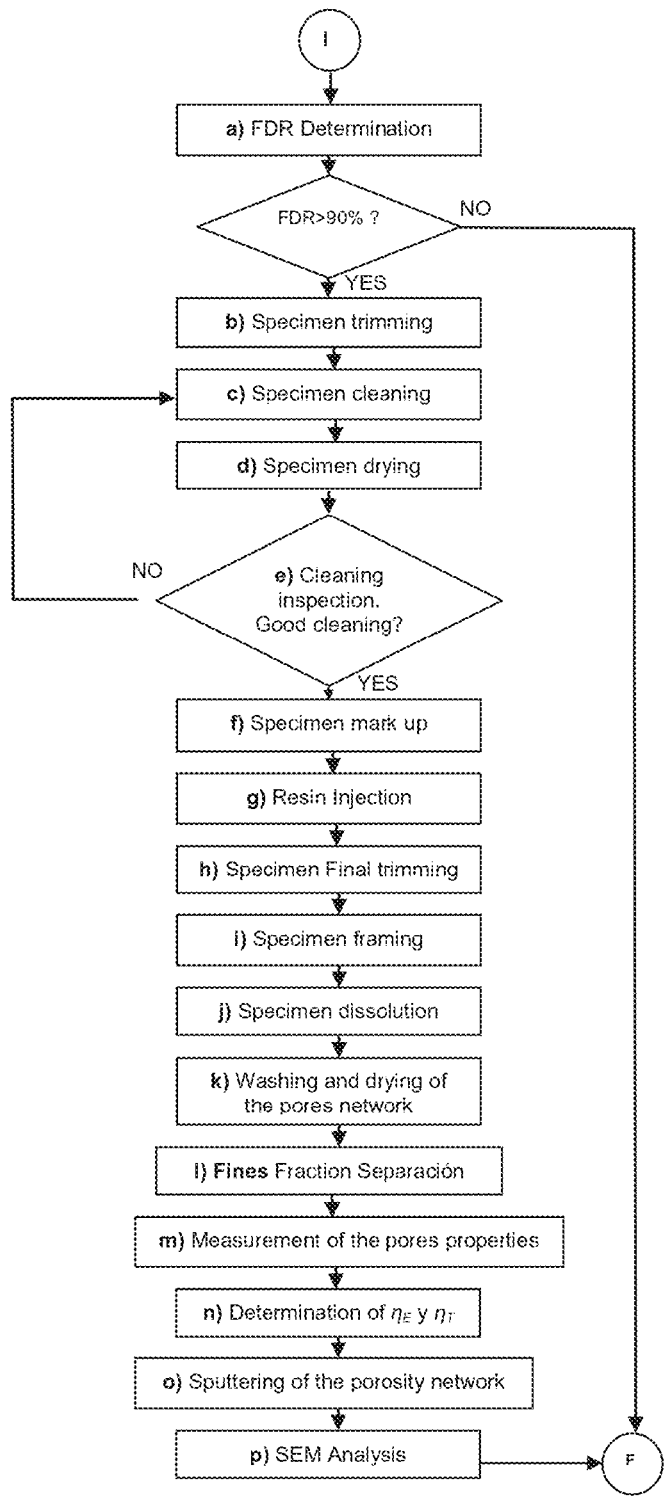
FIG. 1 shows the process flow chart for this invention, to quantitatively determine the effective and total porosity of carbonated sedimentary rocks, plus the morphological characterization of their micro and nanopores.

The present invention refers to a procedure for quantitatively determine both total and effective porosity of carbonated sedimentary rocks (CSR), based on their volumetric and gravimetric properties, plus the morphological characterization of their micro and nanopores (determination of shape, size, and characteristic pattern of their pores networks) applying scanning electron microscopy techniques (SEM).

The quantitative determination of the CSR effective and total porosity is based first, on the elaboration of resin-molds of their pore structure and second, on the determination of the volumetric and gravimetric properties of both the rock specimen and its pore-network mold. Also, the determination of the effective and total porosity is done by the use of original formulae, developed by the inventors of the present invention.

On the other hand, a morphological characterization of micro and nanopores network is done, by applying scanning electron microscopy techniques (SEM), in order to identify relevant properties for permeability analysis of rocks, such as shapes, sizes, connection types, pore-structure patterns and pore-throats, contributing to the estimation of potential recovery efficiency of hydrocarbons.

Following the procedures of this invention, it is possible to determine:
 Volumetric and gravimetric properties required to determine the effective porosity of CSR.
 Effective porosity of CSR.
 Total porosity of CSR.
 The fines fraction existing in CSR specimens.
 Shapes, sizes and pore-network patterns of CSR specimens applying SEM techniques.
 It is also important to mention that:
 The procedure of the present invention focuses on the characterization of pores in the micro and nanometric range, below 10 microns.

The procedure of the present invention involves the dissolution of more than 90% of CSR samples with Hydrochloric acid (HCl) and/or Hydrofluoric acid (HF).

The procedure of the present invention involves the injection or impregnation of resin into the CSR interconnected pores.

The isolated pores of the CSR samples studied are not penetrated by the injected resin.

The procedure of the present invention uses a frame covering the studied CSR specimen all around, to measure the volume of the interconnected pores.

The procedure of the present invention is mainly applied to:

Carbonated sedimentary rocks that can be dissolved in Hydrochloric acid (HCl) and/or Hydrofluoric acid (HF).

The CSR specimens exhibit a Dissolution Factor (FDR) larger than 90%. Even when this analysis is completed with HCl, when the FDR is lower than 90% because of the presence of silicates in the specimen, this can be treated with HF to reach an improved accuracy in the determination of effective porosity.

The procedure of the present invention involves the following steps:

a) Determination of the rock dissolution factor (FDR).
b) Trimming of the rock specimen.
c) Cleaning of the rock specimen.
d) Drying of the specimen.
e) Cleaning inspection.
f) Mark of the specimen for orientation.
g) Resin injection of the specimen.
h) Final trimming of the specimen.
i) Framing of the rock specimen.
j) Dissolution of the rock specimen.
k) Washing and drying of the pores network (pore structure).
l) Determination of the fines fraction.
m) Measurement of the rock pores properties.
n) Determination of effective and total porosity of the rock specimen ($\eta_E$ y $\eta_T$).
o) Sputtering of the porosity network.
p) Analysis with scanning electron microscopy techniques (SEM).

In order to understand better the procedure of this invention, FIG. 1 presents a flow chart that depicts graphically the steps involved to determine both effective and total porosity.

a) Rock Dissolution Factor Determination (FDR):

The dissolution of the rock is numerically expressed as a Rock Dissolution Factor (FDR). The FDR indicates how appropriate is to apply the procedure of the present invention to a rock specimen in order to determine its effective and total porosity, and the morphological characterization of its micro and nanopores.

1. When FDR values are larger than 90% (ninety percent) by weight of the rock, this procedure provides more reliable results.
2. As FDR goes down below 90% (ninety percent) by weight of the rock, it provides less reliable results.

Since the procedure of the present invention deals with carbonated rocks, a 15 to 25 ml concentrated HCl acid dissolution or digestion is performed in a 60 to 70° C. temperature environment, undergoing magnetic shacking for 20 to 40 minutes until the rock is fully solubilized. Next, it is passed through a paper filter in a funnel; the filter paper is previously dried to a constant weight. The filtered fluid is received in a 100 ml volumetric flask. The solids on the filter paper are distilled-water washed and dried for 1 to 2 hours and their weigh recorded (record the amount of sample used and the filtered volume).

From this dissolution, an aliquot is taken to determine the concentration of calcium, magnesium and other materials soluble in HCl as follows:

Calcium:
a. Pour a 20 ml aliquot in an Erlenmeyer Flask.
b. Add 40 ml of KOH 0.5 M solution, shake for 2 minutes, add about 2 ml of Hydroxynaphtoate Blue (from pink changing to blue) or Murexide dye (change from pink to orchid purple).
c. Titrate with EDTA solution (the spent volume is designated as $T_1$) (the concentrate of EDTA solution has to be adequate to the more ideal, it can begin from 0.01 M) the final color change must be hold for at least 20 seconds.
d. The calcium content expressed in percentage can be calculated as:

$$\text{Calcium (\%)} = (T_1 * M * 0.04 * f/m) * 100$$

Where:
$T_1$ is the EDTA volume spent with Hydroxynaphtoate Blue, in milliliters.
M is the molarity of EDTA.
0.04 are the Calcium milliequivalents.
f is the dilution factor equals to graduation ring/aliquot.
m is the sample mass in grams.

Magnesium:
a. Pour a 20 ml aliquot in an Erlenmeyer Flask.
b. Add 5 ml of a pH (NH4Cl—NH4OH) regulating solution, shake for 2 minutes, add about 0.1 mg of Eriochrome Black T.
c. Titrate with EDTA solution (the spent volume is designated as $T_2$) (the concentrate of EDTA solution has to be adequate to the more ideal, it can begin from 0.01 M) the color change will be to red-wine or pink to blue; it must be hold for at least 20 seconds.
d. The calcium content expressed in percentage can be calculated as:

$$\text{Magnesium (\%)} = (0.024(T_2 - T_1) M * f/m) * 100$$

Where
0.024 are the Magnesium milliequivalents.
$T_2$ is the EDTA volume spent with Eriochrome Black T.
The other variables have the meaning described above.

Note:
The Ca and Ng milliequivalents can be changed by their carbonates or being calculated through their conversion factors.

Percentage of HCl Insoluble Material:
a. Use the same solution prepared earlier, pass it through a Whatman paper in a funnel; the filter paper is previously dried to a constant weight.
b. The HCl insoluble solids (materials not soluble in HCl acid) remaining on the Whatman paper are distilled-water washed and dried for 1 hour at 50 to 60° C. temperature.
c. Once the solids are dried they are cooled are weighed.
d. The percentage of insoluble material is calculated with the following formula:

$$\text{\% of Insoluble Material in HCl} = (\text{residues weight}/\text{sample weight}) * 100$$

Finally, the Rock Dissolution Factor (FDR) is calculated as:

$$\text{FDR} = 100 - \text{\% Insoluble material in HCl}$$

b) Trimming of Rock Specimens (Samples):

Trimming of rock specimens for resin injection must consider the following issues:

The amount, in volume, of sample available.

The volume of sample required for injection.

The volume of sample appropriate for scanning electron microscopy analysis (SEM).

The sample trimming geometry must be as regular as achievable to determine its volume as accurate as possible.

It is recommended to use 2.0 cm by 2.0 cm by 2.0 cm cubic specimen sizes before resin injection if there is plenty of rock samples.

c) Specimens Cleaning:

Specimens cleaning is achieved with a Soxtler continuous extraction device for an average of three days long, depending on the type and amount of hydrocarbons in the porous system, and the nature of the rock.

After drying in a convective oven, it must be observed whether there are remaining hydrocarbons in the specimen; this is observed when they "boil" in the porous rock system. If so, more cleaning is required in the Soxtler system.

The solvents used for cleaning in the Soxtler system can be any aromatic hydrocarbon, although those providing the best results are Xylene and Toluene.

Figure 2:
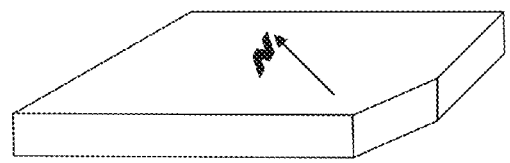
FIG. 2 illustrates a procedure to mark and orientate samples.

Optionally it is possible to request the characterization of the existing hydrocarbons.

d) Drying of Rock Specimens:

Drying of the as-trimmed rock specimens is carried by introducing them in a convective oven for 2 to 4 hours at 60 to 125° C. degrees Celsius.

e) Cleaning Checking:

After specimens drying a check for existence of hydrocarbons must be done while they are hot. If some bubbles come out of the pore system Soxtler cleaning must continue (Steps c and d) until no bubbles are observed during drying.

f) Mark on the Sample for Orientation:

Whenever possible, it is recommended to mark the rock specimen to properly orientate the sample before it is observed and analyzed; to do so, one of the corners of the sample must be conventionally trimmed to define with respect to it the upper and lower sides and the geographical orientation if possible. FIG. 2 depicts a suggested scheme to do it. It is also required to record the orientation and to photograph the as-marked sample.

g) Resin Injection:

Once the specimens are clean, epoxy-resin is vacuum injected into the rocks, this could be acrylic, styrene, vinyl or epoxy based; the thickness of the specimen should be appropriate for:

A Good resin penetration in the specimen.

Being able to expose the faces of the resin-filled specimen by trimming a thin layer of every single one of its faces. Although it means to waste some of the specimen.

h) Trimming of the Resin-Injected Final Specimen:

Here the cut must be done considering the following:

The sectioning must be done with the thinnest sawing disk possible.

Every face of the as injected specimen must be totally uncovered.

Figure 3:
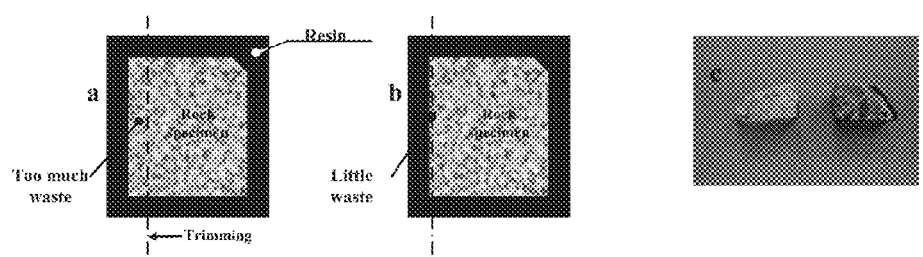
FIG. 3 depicts the trimming of resin-injected rock samples to limit the amount of rock wasted, and their final form.
Figure 4:
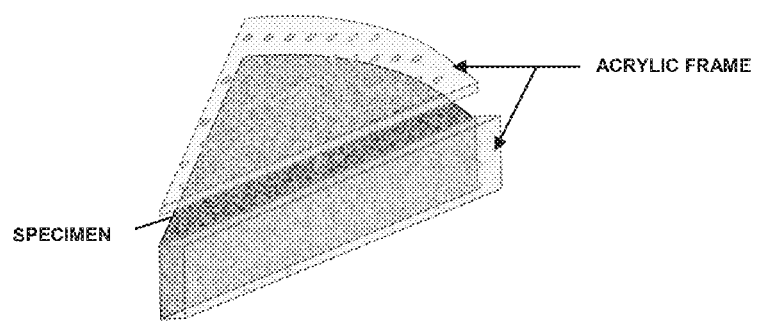
FIG. 4 shows the frame installation scheme.

The trimming of each face of the specimen must be done so that the wasted material may be the least, according to the scheme shown on FIG. 3.

i) Framing of the Acrylic Frame:

In Order to obtain the sample's properties required to determine its effective and total porosity, it has to be completely covered with acrylic plates, as shown on FIG. 4. The framing of the specimen is done considering the following:

Leading orientation of the pores system, if there is such.

The easiness with which the sample may be analyzed with scanning electron microscopy (SEM).

Figure 5:
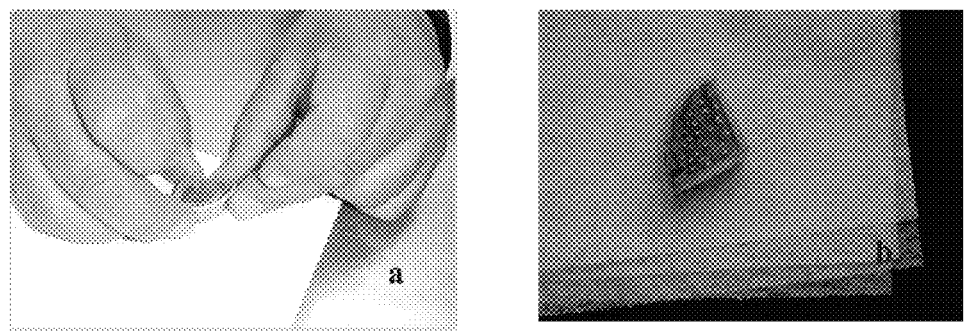
FIG. 5 shows the frame installation procedure.

The need to conserve as much as possible the integrity of the pores structure. It is required to fully cover the specimen with the acrylic plates to determine its effective porosity; small holes on each acrylic plate must be provided to facilitate water and acids flow; contacts between acrylic plates at the corners are cemented with a Hydrochloric acid (HCl) and/or Hydrofluoric acid (HF) resistant adhesive, as illustrated on FIG. 5.

j) Dissolution of the Rock Specimen:

Highly carbonated rocks dissolution is achieved by introducing the framed specimen in a Griffin beaker; next, the sample is completely covered with HCl, having a concentration between 1 and 100%. The reaction is keep for a period within hours to one day, to completely dissolve the rock. This time will depend upon the rock's reactivity; although this period can be extended until reaching full dissolution. For rocks containing Silicate oxide ($SiO_2$), first it is recommended to dissolve with HF and then with HCl, in concentrations ranging from 10 to 100% for both acids.

k) Washing and Drying of the Pores Structure (Pore Structure):

Once the rock is fully dissolved, the remaining material in the frame is the pores-structure cast in resin, impregnated with HCl. This should be washed to eliminate any solid residuals and the acid as well, following the next steps:

The acrylic frame is carefully laid on a Petri dish.

Drops of deionized water are allowed to fall over the pores structure to wash it, this to minimize the risk of damage.

Figure 6:
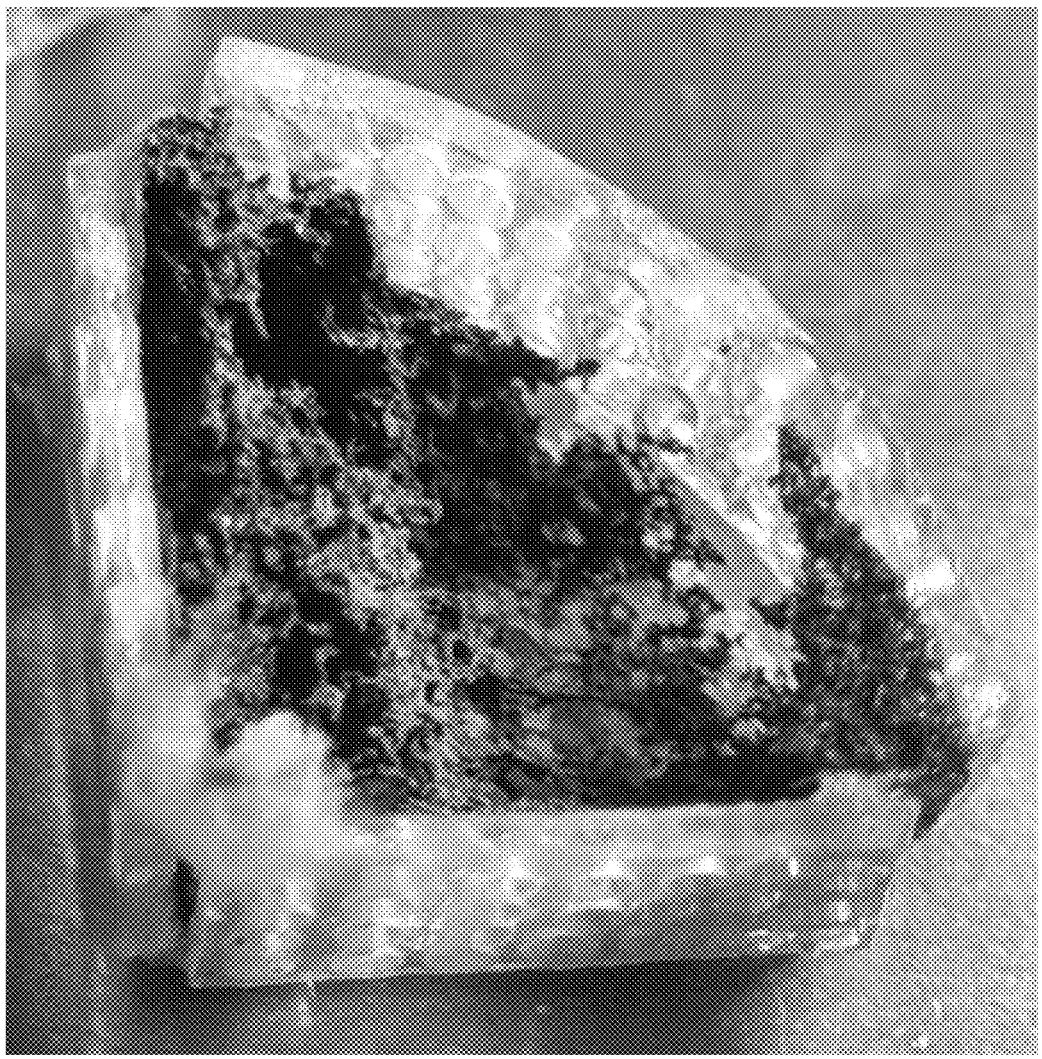
FIG. 6 shows the pores structure inside the frame.

Once the pore structure is well washed, it is dried in a desiccator for a day at least, to make sure that there are neither drops nor thin films of water. Air drying is not recommended since environmental humidity can add water to the pores structure. The use of a desicator is important since it helps to maintain the integrity of the pores resin-cast. The final result is the interconnected pores structure, adhered to the walls of the acrylic frame, as shown in FIG. 6.

l) Fines Fraction Separation:

After washing the acrylic frame with the pores structure inside, the solid residues are collected, they contain both, the non-connected pores-casts and existing fine materials. These two different residues are separated by agitation and decantation in a second step. The data obtained from these two sets of materials complete the information required to determine both the effective and total porosity of the rock specimen.

m) Measurement of the Rock Pores Properties.

In order to determine the volume of the pores structure in the rock specimen, it is needed to define the following variables, where "rock" means rock specimen being tested:

$m_r$=rock mass (mass of solids of the rock, without fines).

$m_f$=fines mass in the rock.

$m_E$=mass of resin in the effective porosity.

(mass of resin filling the interconnected pores, effective porosity).

$m_{NE}$=mass of resin in the non-effective porosity.

(mass of resin filling the non-interconnected pores, non-effective porosity).

$m_R=m_{r+f+E}$=mass of rock injected with resin, mass of (rock+fines+resin in effective porosity).

$m_{B+A}$=mass of (acrylic frame+adhesive).

$m_{B+A+E}$=mass of (acrylic frame+adhesive+resin in effective porosity).
$m_T$=$m_{R+B+A}$=mass of (resin injected rock+acrylic frame+adhesive).
$m_p$=mass of clean filter paper.
$\rho_r$=rock density.
(Density of solids integrating the rock, without fines).
$\rho_f$=density of fines contained in the rock.
$\rho_E$=$\rho_{NE}$=density of resin filling the rock pores system.
$\rho_R$=$\rho_{r+f+E}$=density of the rock specimen injected with resin.
density of (rock+fines+resin in the effective porosity).
$\rho_{B+A+E}$=density of (acrylic frame+adhesive+resin in the effective porosity).
$\rho_T$=$\rho_{R+B+A}$=density of (rock specimen injected with resin+acrylic frame+adhesive).
$\rho_p$=density of the clean filter paper.
$\rho_{p+f}$=density of (filter paper+fines).
$V_r$=Rock Volume.
(Volume of solids integrating the rock, without fines).
$V_f$=Volume of fines contained in the rock.
$V_E$=Volume of resin in the effective porosity.
(Volume of resin filling the interconnected pores, effective porosity).
$V_{NE}$=Volume of resin in the non-effective porosity
(Volume of resin filling the non-connected pores, non-effective porosity).
$V_V$=$V_E$+$V_{NE}$=Total Volume of resin injected pores
(Volume of resin in the effective porosity+volume of resin in the non-effective porosity).
$V_R$=Volume of the rock injected with resin,
Volume of (rock+fines+resin in the effective porosity).
$V_{B+A}$=Volume of (acrylic frame+adhesive).
$V_{B+A+E}$=Volume of (acrylic frame+adhesive+resin in the effective porosity).
$V_T$=$V_{R+B+A}$=Volume of (rock injected with resin+acrylic frame+adhesive).

Figure 7:
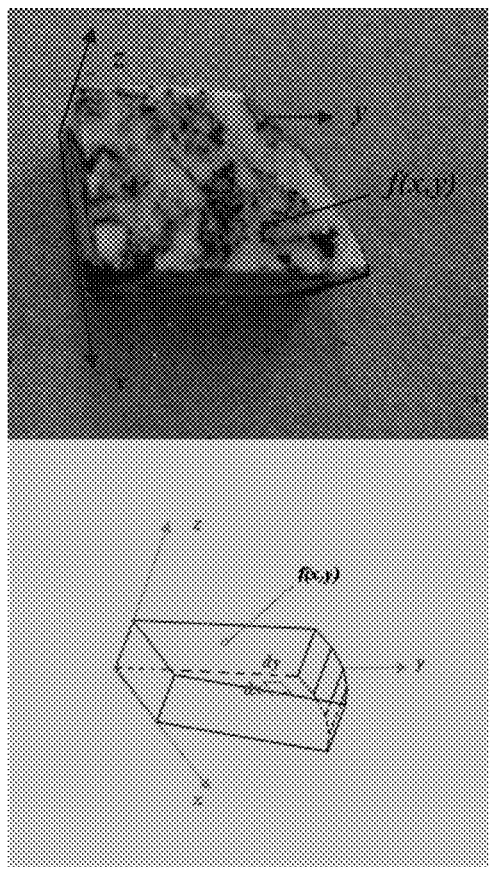
FIG. 7 depicts the rock specimen in a coordinate system.

The volume of the injected rock specimen is determined according to the following fundamental statement:

It is considered an specimen $\Omega$, as the one depicted in FIG. 7. This element occupies a region in the space (x,y,z).

One of the specimen faces occupies a region R in the (x,y) plane. The upper boundary of $\Omega$ is limited by the function f(x,y), then the volume occupied by $\Omega$ is given by $$V = \iint_R f(x, y) dx dy$$

The above expression assumes that the element is non-porous.

The corresponding masses area measured with a high precision analytic balance.

Determination of densities is done using an Auto Pycnometer, preferably with a working range of 0.0 to 19.9 g/cm³, and at least one thousandth of g/cm3 precision, applying the ASTMD10-29 method.

Mass determination is done using a precision analytical balance with a working range of 0 to 160 grams, and a precision of at least 0.0001 grams.

n) Determination of the Effective and Total Porosity of a Rock Specimen ($\eta_E$ y $\eta_T$):

I. Effective Porosity Calculation, $\eta_E$:
The effective porosity is determined using the following expression:

$$\eta_E = \frac{\left(\frac{m_E}{\rho_E}\right)}{\left(\frac{m_r}{\rho_r} + \frac{m_f}{\rho_f} + \frac{m_E}{\rho_E}\right) + V_{NE}} \quad (1)$$

II. Total Porosity Calculation, $\eta_T$:
The total porosity is determined using the following expression:

$$\eta_T = \frac{V_E + V_{NE}}{V_E + V_r + V_f + V_{NE}} \quad (2)$$

III. Fine Fraction Volume Determination in the Sample, $V_f$:
After dissolution of the rock, a fine material is collected in a dried and weighted filter paper, as described in step I) Fines fraction separation.
Density of filter paper is obtained in both conditions, alone and with fine residues on it. Besides, since their respective masses were already obtained, the expression to determine the fine fraction of the sample is as follows:

$$V_f = \frac{m_f + m_p}{\rho_{f+p}} - \frac{m_p}{\rho_p} \quad (3)$$

Observe that expressions (1) and (2) consider the volume of spaces injected by the resin, $V_v$=$V_E$+$V_{NE}$, is the total volume of voids in a rock sample, i.e.,
Here, $$V_V = \lim_{\substack{\Delta x \to 0 \\ \Delta y \to 0 \\ \Delta z \to 0}} \sum \sum_\Omega \sum \Delta z \cdot \Delta y \cdot \Delta x = \iiint_\Omega dz \cdot dy \cdot dx \quad (4)$$

Here, $$V_V = \lim_{\substack{\Delta x \to 0 \\ \Delta y \to 0 \\ \Delta z \to 0}} \sum \sum_\Omega \sum \Delta z \cdot \Delta y \cdot \Delta x \quad (5)$$

Figure 8:
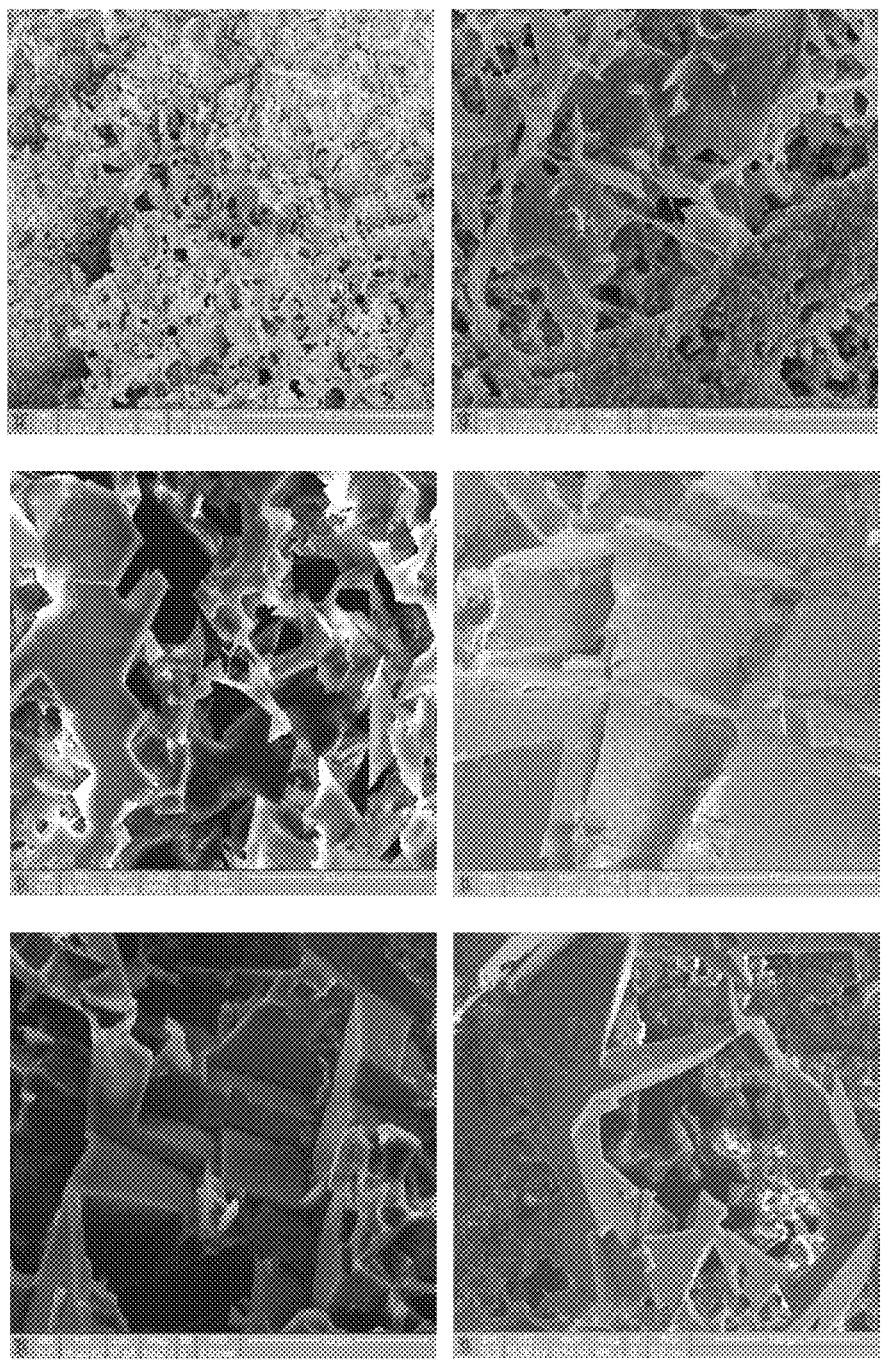
FIG. 8 illustrates examples of pores networks, made of epoxy resin, and obtained from carbonated rock specimens.

Is the sum of all differential voids existing in volume $\Omega$ of the studied rock specimen. Expressions (1) and (2) are exact; however, in practice this consideration is approximated since there are isolated pores inside the rock, to which the resin does not reach. It should be noticed that this limitation is shared with other methods based on fluids injection (gases and Hg), since neither of these penetrate fully isolated pores.

o) Sample Sputtering:
Here, the acrylic frame already contains both, a resin-replica of the pores structure and empty fractures existing in the rock specimen, for this reason and to carefully study these structures, it is needed to cover it with a very thin film of conductive material such as carbon, gold or palladium-gold. Also, because of the three dimensional nature of the pores structure, it is recommended to cover it in three different directions to include all pores and channels. The observation of these samples allows appreciating relevant morphologic and topographic characteristics of pores and channels.

p) Observation by Scanning Electron Microscopy (SEM):
Once the pores structure is covered with an electrons conductive-film, it is ready to be studied with a SEM to determine shapes, measure special features such as pore throats and to identify pores structure patterns inside the rock specimen. This is done in a High Resolution Scanning electron microscope (HR-SEM). FIG. 8 shows several examples of pores networks, obtained from rock specimens, with HR-SEM.

In summary, the procedures of the present invention are mainly applied to:
1. Rock samples soluble in HCl and/or HF, although experience indicates that carbonated rocks satisfactorily dissolve in HCl.
2. The size of the specimens is about five cubic centimeters (6 cm$^3$).
3. The smallest porosity diameter were resin has been injected is 35 nanometers.

Also, the present invention provides the following original contributions:
1. A novel formula to calculate the effective microporosity in the volume of the rock specimen, based on its mass, density and volume before and after setting up an acrylic frame on the resin injected rock specimen, i.e.:
   a. Volume of the specimen with resin inside its porous system.
   b. Mass of the rock specimen including the resin inside its porous system.
   c. Density of the specimen with resin inside its porous system.
   d. Mass of the acrylic frame plus adhesive, used to encapsulate the specimen.
   e. Mass of the resin occupying the intercommunicated voids inside the specimen.
   f. Volume of acrylic frame plus adhesive used to encapsulate the specimen.
   g. density of the acrylic frame plus adhesive plus resin inside the specimen porous system
2. The mass and density properties are measured in a matter of minutes.
3. The interconnected porosity of the rock specimen is measured quickly and accurately.
4. The interconnected pore structure is integrally kept.
5. It uses a method based on chemical analysis to evaluate the rock sample solubility to estimate the accuracy with which the effective porosity will be determined.
6. The careful morphologic characterization of the pores in a rock is key factor to reliably determine relevant properties of hydrocarbons reservoirs. Thus, this characterization must be supported on both, an accurate model of the pores structure and its interconnections, as well as on precise procedures to measure pores and throats.

Additional to the determination of effective porosity, the present invention allows determining the following parameters at the micro and nanometer scale, through scanning electron microscopy (SEM):

Length, diameter and shapes of pores.

Pore throats diameters and shapes.

Porosity patterns.

Pore/throat connections.

Type and degree of heterogeneity.

Roughness of pores walls.

Roundness of pores.

Relative orientation of pores.

Additionally, the pores structure can be morphologically characterized in the three dimensional cast of the pore network, rotating or tilting it, as it is usually done.

EXAMPLES

To have a better understanding of the present invention, some practical examples are described next; although this will not limits its scope.

Example 1

Three samples of carbonated rocks obtained at different depths below the sea floor, in the marine zone of the Gulf of Mexico (GOM), at the Sonda de Campeche Area, were tested in step a) of the present invention, "Determination of the rock dissolution factor (FDR)".

An acid dissolution of the rock samples was done using 20 ml of concentrated HCl, at 60 to 70 degrees Celsius and magnetic shaking for 30 minutes until the samples were fully dissolved. Next, the solution was funnel filtered with a filter paper previously brought to constant weight. The filtered fluid was received in a 100 ml volumetric flask. The solids on the filter paper were distilled-water washed and dried for 1.5 hours and its weigh was recorded; it was recorded the amount of sample used to the flask volume-mark. The results obtained are presented in Table 1.

TABLE 1

FDR analysis results of rock samples, obtained from the Gulf of Mexico Marine region.

| Specimen | Laboratory ID | "C" Sample initial weight (g) | "B" Filter paper weight (g) | "A" Filter paper + Residues (g) | Residues weight (g) | Material insoluble in HCl (%) | FDR (%) |
|---|---|---|---|---|---|---|---|
| Dolomite C12B | 1 | 0.5022 | 0.8570 | 0.8707 | 0.0137 | 2.7280 | 97.2720 |
| N/identification | 5 | 0.5025 | 0.8892 | 1.1935 | 0.3043 | 60.5572 | 39.4428 |
| Shale | 6 | 0.5038 | 0.8974 | 1.3008 | 0.4034 | 80.0715 | 19.9285 |

% insoluble Material in HCl = ([A − B]/C) * 100
FDR = 100 − % Insoluble Material in HCl Results on Table 1, show that application of the procedures of the present invention is more reliable for Dolomite C12B and less trustworthy for the two remaining samples.

Example 2

Three specimens of carbonated sedimentary rocks, obtained from the Sonda de Campeche Area, were subjected to the procedures of the present invention, steps a) "Determination of the rock dissolution factor (FDR)" through p) Analysis with scanning electron microscopy techniques (SEM), as it was described in the chapter "Detailed description of the invention" underlining the following issues to determine their effective and total microporosity, as well as their corresponding fines fractions.

FDR determination (Step a) was done just as described in Example 1,

In step b) Trimming of the rock specimen, the samples used were 2 cm by 2 cm by 2 cm, before resin injection.

The specimens cleaning, step c), was done with a Soxhlet extraction column and both Xylene and Toluene.

The specimens drying, step d), was done at 100-125° C., for three hours in a convective oven.

Cleaning checking, step e), was done with the specimens still hot, until no more oil boiling was observed in the pores after drying.

Step f) Mark of the specimen for orientation. Marks on the specimen were made for relative orientation when observed with SEM.

Resin injection, step g), was done with epoxy-resin commercially known as EpoThin No. 20-8140-128, with a catalyst Epoxy Hardener No. 20-8142-016, both from Bluehler.

Final trimming of the specimen, step h), was done with the thinnest sawing disk and their injected faces fully uncovered.

Framing of the rock specimen, step i), was finished by fully wrapping the specimen with an acrylic frame having small holes on each acrylic plate to facilitate water and acids flow; contacts between acrylic plates at the corners were cemented with a Hydrochloric acid (HCl) resistant adhesive.

Dissolution of the rock specimens, step j), was done with 20% diluted HCl inside an extraction chamber.

In step k; Washing and drying of the pores network (pore structure), deionized water dropping washing of the pore network was done in order to eliminate any risk of pore structure damage; drying was done using a desiccator, making sure that no drops or water films were there. The final output is the interconnected pore structure, inside the acrylic frame.

Determination of the fines fraction, step l), was done by shaking, sedimentation and decantation.

In step m), Measurement of the pores network properties, determination of densities was completed by using a Micrometrics Autopicnometer, model 1320, with a 0.0 to 19.9 g/cm³ operation range and 0.001 g/cm³ accuracy. This was done following the ASTMD10-29 method. Also, the masses determination was accomplished using a Metier analytical balance, model AE160, with 0.000 to 160 grams operation range and 0.0001 grams accuracy.

The effective and total porosities calculations, step n), were done applying the following expressions:

$$\eta_E = \frac{\left(\frac{m_E}{\rho_E}\right)}{\left(\frac{m_r}{\rho_r} + \frac{m_f}{\rho_f} + \frac{m_E}{\rho_E}\right) + V_{NE}} \quad (1)$$

$$\eta_T = \frac{V_E + V_{NE}}{V_E + V_r + V_f + V_{NE}} \quad (2)$$

The fine fraction volume was calculated using the following formula:

$$V_f = \frac{m_f + m_p}{\rho_{f+p}} - \frac{m_p}{\rho_p} \quad (3)$$

During step o), Sputtering of the porosity network, the acrylic frame has already a resin-made replica of the pores network and factures existing in the rock specimen. Then, it was covered with a conductive gold thin film in three directions to include all pores and channels.

In step p), Analysis with scanning electron microscopy techniques (SEM), once the pore network was gold covered; it was introduced into a FEI-Nova Nanolab 200 Scanning Electron Microscope chamber to determine shapes, measure features such as pore throats and to identify pore networks patterns inside the rock specimen studied.

Figure 9:
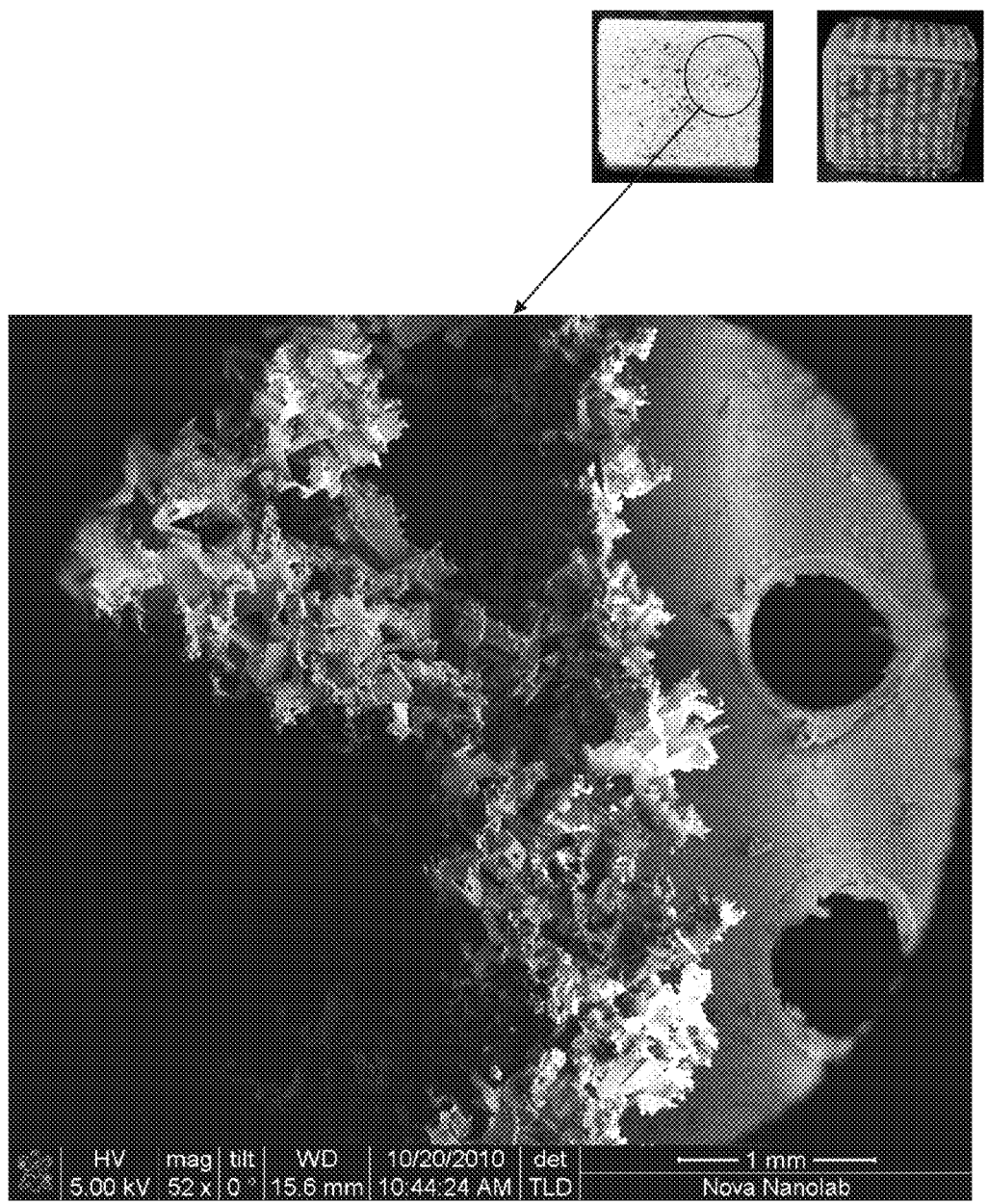
FIG. 9 shows the effective porosity of a rock specimen, supported by a frame.
Figure 10:
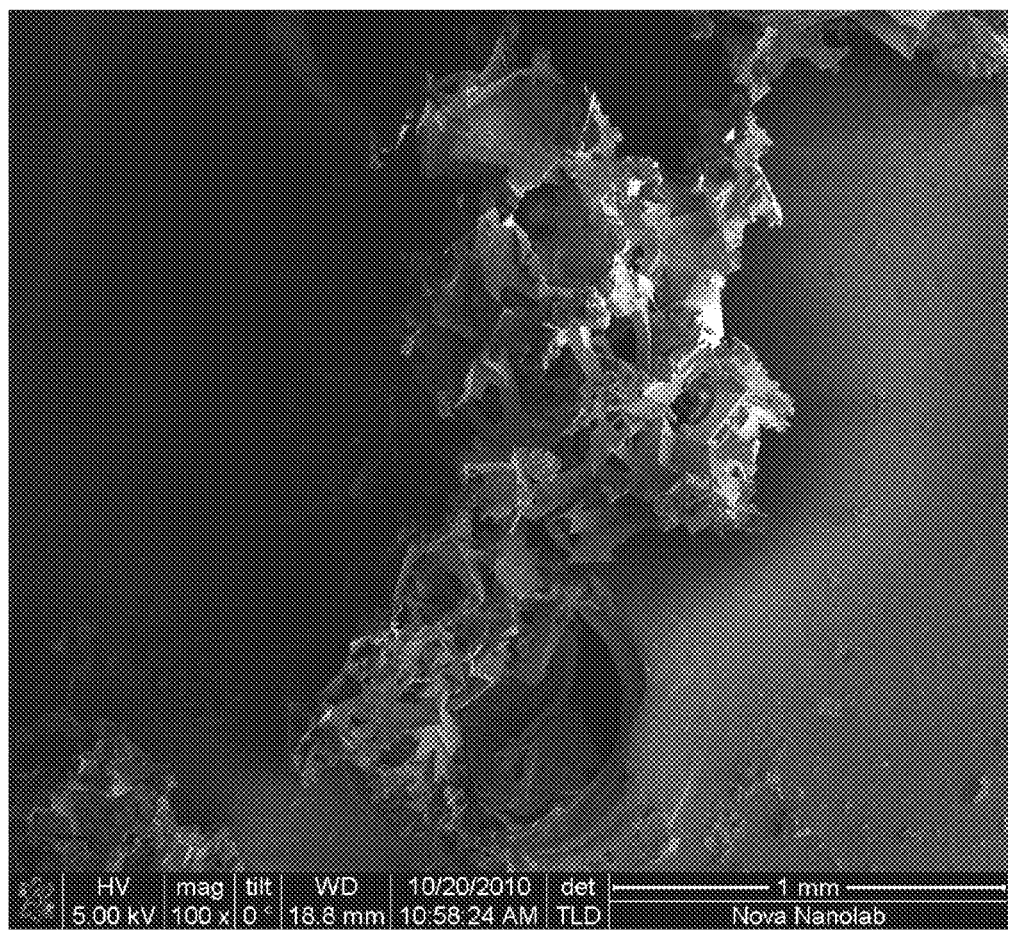
FIG. 10 shows a micrograph of effective porosity obtained from sample 5 (M5).
Figure 11:
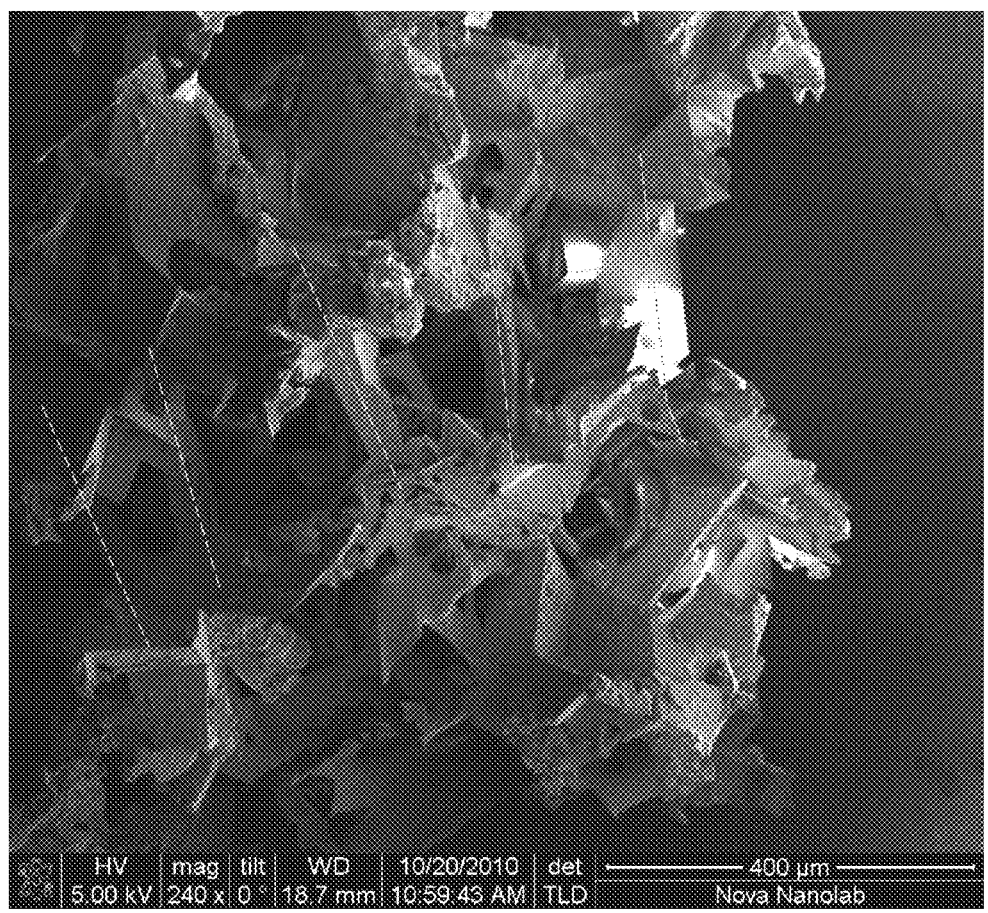
FIG. 11 shows morphological details in an effective porosity network.
Figure 12:
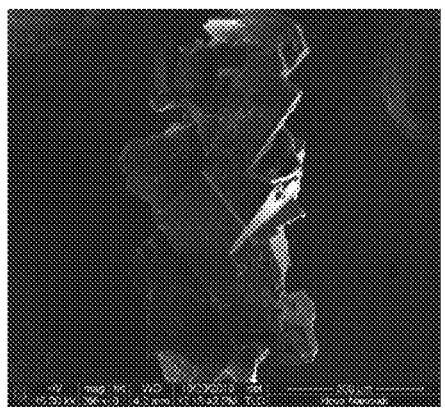
FIG. 12 shows non-connected pores micrographs (non-effective porosity).
Figure 12:
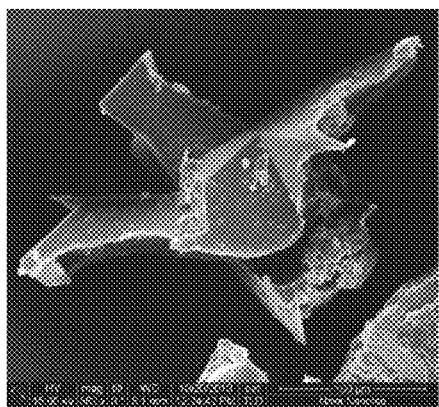
Figure 12:
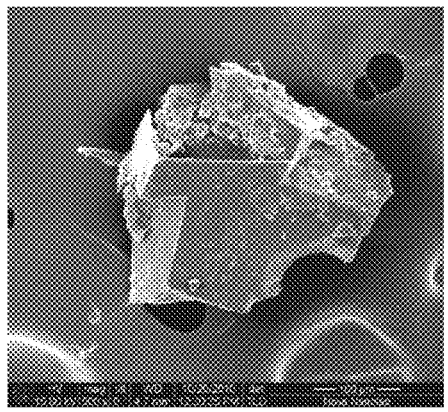
Figure 12:
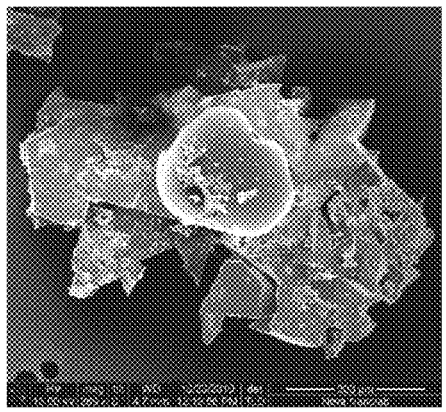
Figure 13:
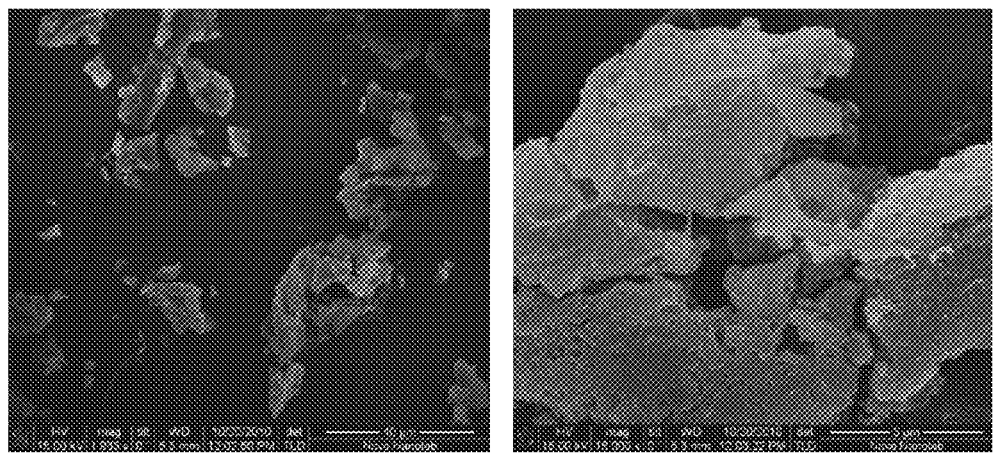
FIG. 13 presents the fraction found during dissolution and chemical analysis results describing the constituent materials.
Figure 13:
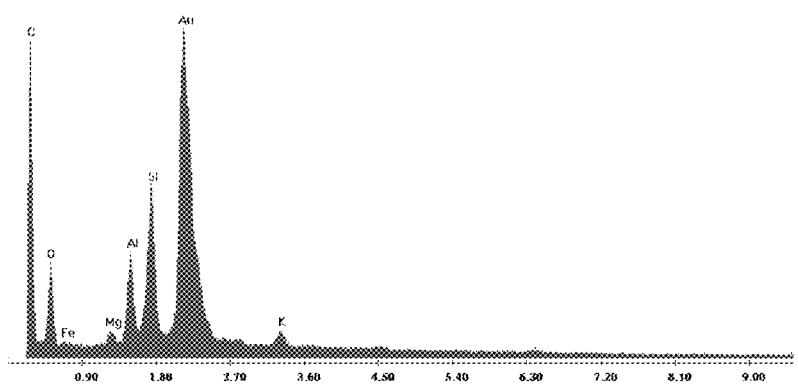

The following results are presented as evidence of the realization of these examples:

Effective porosity supported in the acrylic frame (FIG. 9),

Effective porosity of sample No. 5 (FIG. 10),

Effective Porosity morphology detail (FIG. 11), where pore throats oriented in a similar direction are observed (dotted line), Non-connected pores micrographs (non-effective porosity), in FIG. 12 and The fine fraction found during dissolution (FIG. 13); The inset is an EDX analysis showing that these fines correspond to clayey materials.

The summary of results obtained for these specimens is presented on Table 2.

TABLE 2

Summary of results obtained from the application of the present invention to specimens of carbonated sedimentary rocks, sampled at the Sonda de Campeche, to determine effective and total microporosities and fines fraction.

Figure 14A:
FIGS. 14A, 14B, 14C, 14D and 14E show each of the samples of Table 2.
Figure 14B:
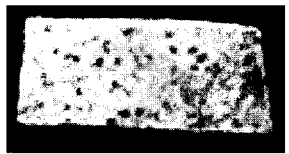
Figure 14C:
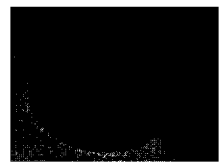
Figure 14D:
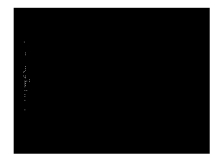
Figure 14E:
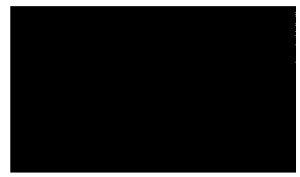

| | Clean samples before resin penetration (FIG. 14A) | | Samples resin injected and dry (FIG. 14B) | | Injection-resin (FIG. 14C) | | Samples injected and dry with acrylic frame (FIG. 14D) | | Samples after dissolution with acrylic frame (FIG. 14E) | | | Fine fraction plus non-connected pores after dissolution | |
|---|---|---|---|---|---|---|---|---|---|---|---|---|---|
| Sample | Density $\rho_r$ g/cm3 | Mass $m_{ri}$ gr | Density $\rho_R$ g/cm3 | Mass $m_R$ gr | Density $\rho_E = \rho_{NE}$ g/cm3 | Mass gr | Density $\rho_{R+B+A}$ g/cm3 | Mass $m_{R+B+A}$ gr | Density $\rho_{B+A+E}$ g/cm3 | Mass $m_{B+A+E}$ gr | Sample | Mass $m_{NE}$ gr | Mass $m_f$ gr |
| M3 | 2.7726 | 6.8877 | 2.7580 | 4.5126 | | | 2.2109 | 5.6032 | 1.2008 | 1.0960 | M3 | 0.00335 | 0.00055 |
| M4 | 2.7623 | 11.2985 | 2.7507 | 7.7765 | | | 2.2763 | 9.3236 | 1.1860 | 1.5570 | M4 | 0.00845 | 0.00775 |
| M5 | 2.7657 | 13.6277 | 2.7478 | 9.8462 | | | 2.2602 | 11.8766 | 1.2092 | 2.0988 | M5 | 0.0052 | 0.0103 |
| R1 | | | | | 1.1301 | 2.0048 | | | | | | | |
| R1-bis | | | | | 1.1318 | 3.3682 | | | | | | | |

TABLE 2-continued

Summary of results obtained from the application of the present invention to specimens of carbonated sedimentary rocks, sampled at the Sonda de Campeche, to determine effective and total microporosities and fines fraction.

Average 1.13095

| | Mass | | Fractions Volumes | | | | Porosity | |
|---|---|---|---|---|---|---|---|---|
| | Connected Pores | Solids in the rock | Non Connected Pores | Connected Pores | Solids in the rock | Fines in the rock | | |
| Sample | $m_E$ gr | $m_r$ gr | $V_{NE}$ cm3 | $m_E/\rho_E$ cm3 | $m_r/\rho_r$ cm3 | $m_f/\rho_f$ cm3 | Efective $n_E\%$ | Total $n_T\%$ |
| M3 | 0.0054 | 4.50665 | 0.002962 | 0.00477 | 1.62542 | 0.00046 | 0.29 | 0.47 |
| M4 | 0.0099 | 7.75885 | 0.007472 | 0.00875 | 2.80884 | 0.00561 | 0.31 | 0.57 |
| M5 | 0.0684 | 9.7675 | 0.004598 | 0.06048 | 3.53166 | 0.0045 | 1.68 | 1.81 |

Note: R1 and R1-bis correspond to the densities of two specimens of the same resin.
FDR = 97.66%

The studied samples allow observing the following:
a. Effective porosity is less than the corresponding total one.
b. Samples M3 and M4 provide similar results, whereas result of M5 are different, this is because their properties are different, as it can be observed on Table 2.

The invention claimed is:

1. A process to quantitatively determine effective and total porosity of carbonated sedimentary rocks, and morphologic characterization of their micro and nanopores, which comprises obtaining specimens of carbonated sedimentary rock and subjecting the carbonated sedimentary rock specimens to:
  a. Determining rock dissolution factor (FDR) of a carbonated sedimentary rock specimen,
  b. Trimming a carbonated sedimentary rock specimen to obtain a trimmed rock specimen,
  c. Cleaning the trimmed rock specimen to obtain a cleaned rock specimen,
  d. Drying the cleaned rock specimen to obtain a dried rock specimen,
  e. Inspection of the cleaned rock specimen to obtain an inspected rock specimen,
  f. Marking of the cleaned rock specimen for orientation to form a marked rock specimen,
  g. Injecting a resin into the marked rock specimen to form a resin-injected rock specimen,
  h. Trimming the resin injected rock specimen,
  i. Framing of the resin injected rock specimen,
  j. Dissolving the resin injected rock specimen to form a pore network specimen having a resinous pore structure,
  k. Washing the pore network specimen and collecting the solid residues containing non-connected pores-casts and existing fines material, and drying the pore network specimen,
  l. Separating the non-connected pores-casts from the existing fine material, and determining the mass of the non-connected pores-casts and of the existing fine material,
  m. Measurement of the pore structure properties of the pore network specimen,
  n. Determination of effective and total porosity of the pore network specimen ($\eta_E$ and $\eta_T$),
  o. Sputtering of the pore network specimen, and
  p. Analysis of the pore network specimen with scanning electron microscopy to characterize the porosity of the pore network specimen in the range of scale sizes from micrometric to nanometric.

2. The process of claim 1, wherein the resin-injected rock specimen is dissolved in step (j) with HCl and/or HF.

3. The process of claim 1, wherein step (a) comprises acid dissolution or digestion of the specimen using 15 to 25 ml of concentrated HCl, at 60 to 70° C. temperature and magnetic shaking for 20 to 40 minutes until the rock is completely dissolved to obtain a rock solution, the rock solution is filtered to obtain separated solids, which separated solids are water washed, dried and weighed, and the rock dilution factor (FDR) of the separated solids is determined by the formulae % of Insoluble material in HCl=(residues weight/sample weight)*100 and

FDR=100−% Insoluble material in HCl.

4. The process of claim 1, wherein the specimens of carbonated sedimentary rock have a Rock dissolution factor larger than 90%.

5. The process of claim 1, wherein the rock specimens obtained in step (b) have the following dimensions: 2.0 cm by 2.0 cm by 2.0 cm.

6. The process of claim 1, wherein an aromatic hydrocarbon is used as a solvent in step (c) to clean the rock specimen.

7. The process of claim 6, wherein the aromatic hydrocarbon used in step (c) is xylene or toluene.

8. The process of claim 1, wherein step (d) is conducted in a convection oven for 2 to 4 hours at 60 to 125° C.

9. The process of claim 1, wherein step (e) is conducted while the cleaned rock specimen is hot.

10. The process of claim 1, wherein step (f) comprises trimming the sample to orient it.

11. The process of claim 1, wherein an acrylic, styrene, vinyl or epoxy based resin is injected in step (g).

12. The process of claim 1, wherein every face of the injected rock specimen is totally uncovered.

13. The process of claim 1, wherein the resin-injected rock specimen is completely covered with perforated acrylic plates in step (i).

14. The process of claim 1, wherein step (j) is conducted with hydrochloric acid (HCl) having a concentration of 1 to 100%.

15. The process of claim 1, wherein the resin-injected rock specimen of step (j) contains silicon dioxide, and dissolution is conducted by first diluting with hydrofluoric acid and then with hydrochloric acid in concentrations in the range 10 to 100% for each acid.

16. The process of claim 1, wherein step (k) is conducted by washing the pore network specimen by drop-falling deionized water, and then drying in a desiccator for at least a day.

17. The process of claim 1, wherein step (l) comprises separation of the fines fraction by agitation and decantation of fine materials from the non-connected pore network specimen.

18. The process of claim 1, wherein determination of densities of the pore network specimen in step (m) is conducted with an Auto Pycnometer with a working range of 0.0 to 19.9 g/cm$^3$, and at least one thousandth of g/cm$^3$ precision.

19. The process of claim 1, wherein in step (m), mass determination is conducted using a precision analytical balance with a working range of 0 to 160 grams, and a precision of at least 0.0001 grams.

20. The process of claim 1, wherein in step (n), the determination of effective porosity ($\eta_E$) is conducted using the following expression (1):

$$\eta_E = \frac{\left(\frac{m_E}{\rho_E}\right)}{\left(\frac{m_r}{\rho_r} + \frac{m_f}{\rho_f} + \frac{m_E}{\rho_E}\right) + V_{NE}} \quad (1)$$

Where:
$m_r$=rock mass
(mass of solids of the rock, without fines)
$m_f$=fines mass in the rock
$m_E$=mass of resin in the effective porosity
(mass of resin filling the interconnected pores, effective porosity)
$\rho_r$=rock density
(Density of solids integrating the rock, without fines)
$\rho_f$=density of fines contained in the rock
$\rho_E=\rho_{NE}$=density of resin filling the rock pores system.

21. The process of claim 1, wherein in step (n), the determination of total porosity ($\eta_T$) is conducted using the following expression (2):

$$\eta_T = \frac{V_E + V_{NE}}{V_E + V_r + V_f + V_{NE}} \quad (2)$$

Where:
$V_r$=Rock Volume
(Volume of solids integrating the rock, without fines)
$V_f$=Volume of fines contained in the rock
$V_E$=Volume of resin in the effective porosity
(Volume of resin filling the interconnected pores, effective porosity)
$V_{NE}$=Volume of resin in the non-effective porosity
(Volume of resin filling the non-connected pores, non-effective porosity).

22. The process of claim 1, wherein in step (n), the determination of the fines fraction ($V_f$) is conducted using expression (3):

$$V_f = \frac{m_f + m_p}{\rho_{f+p}} - \frac{m_p}{\rho_p} \quad (3)$$

Where:
$m_f$=fines mass in the rock
$m_p$=mass of clean filter paper
$\rho_p$=density of the clean filter paper
$\rho_{p+f}$=density of (filter paper+fines).

23. The process of claim 1, wherein in step (p), determination of shapes, measurement of special features including pore throats and identification of pores-structure patterns of the rock specimen are conducted in a High Resolution Scanning electron microscope (HR-SEM).

24. The process of claim 1, wherein the analysis of the pore network specimen with scanning electron microscopy characterizes the porosity of the pore network specimen of carbonated sedimentary rocks in the range below ten (10) microns.

* * * * *